(12) United States Patent
Wataya et al.

(10) Patent No.: US 10,191,271 B2
(45) Date of Patent: Jan. 29, 2019

(54) IMAGE PICKUP SYSTEM

(71) Applicant: OLYMPUS CORPORATION, Tokyo (JP)

(72) Inventors: Yuichi Wataya, Akiruno (JP); Hirohiko Matsuzawa, Hino (JP); Masahiro Kawauchi, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 146 days.

(21) Appl. No.: 15/455,213

(22) Filed: Mar. 10, 2017

(65) Prior Publication Data

US 2017/0184838 A1 Jun. 29, 2017

Related U.S. Application Data

(63) Continuation of application No. PCT/JP2015/075082, filed on Sep. 3, 2015.

(30) Foreign Application Priority Data

Oct. 6, 2014 (JP) ................................ 2014-205855

(51) Int. Cl.
*G02B 23/24* (2006.01)
*A61B 1/00* (2006.01)
(Continued)

(52) U.S. Cl.
CPC ............ *G02B 23/2484* (2013.01); *A61B 1/00* (2013.01); *A61B 1/00009* (2013.01);
(Continued)

(58) Field of Classification Search
CPC .. G02B 23/2484; G02B 23/2461; A61B 1/04; A61B 1/0638; A61B 1/00045;
(Continued)

(56) References Cited

U.S. PATENT DOCUMENTS

| 5,803,900 | A | 9/1998 | Matsumoto et al. |
| 7,236,196 | B1 * | 6/2007 | Oda ........................ H04N 9/045 348/283 |

(Continued)

FOREIGN PATENT DOCUMENTS

| JP | H10-170840 A | 6/1998 |
| JP | 2007-020728 A | 2/2007 |

(Continued)

OTHER PUBLICATIONS

International Search Report dated Nov. 2, 2015 issued in PCT/JP2015/075082.

*Primary Examiner* — Tung T Vo
(74) *Attorney, Agent, or Firm* — Scully, Scott, Murphy & Presser, P.C.

(57) ABSTRACT

An image pickup system includes a light source apparatus, an objective optical system, an image pickup device, a judging portion configured to judge: an object is observed in which of a distant view and a near view, and an image pickup control portion configured to set a reading mode of the image pickup device according to a judgment result of the judging portion. The light source apparatus is capable of sequentially emitting red light, green light and blue light. The image pickup control portion sets a single pixel reading mode when that the object is observed in the distant view is judged, and blue light is emitted from the light source apparatus, and sets to a pixel addition reading mode when that the object is observed in the distant view is judged, and red light is emitted from the optical apparatus.

18 Claims, 7 Drawing Sheets

(51) Int. Cl.
| | |
|---|---|
| *A61B 1/04* | (2006.01) |
| *A61B 1/06* | (2006.01) |
| *H04N 5/347* | (2011.01) |
| *H04N 5/378* | (2011.01) |
| *H04N 9/04* | (2006.01) |
| *H04N 9/07* | (2006.01) |
| *H04N 5/225* | (2006.01) |
| *H04N 5/235* | (2006.01) |

(52) U.S. Cl.
CPC ............ *A61B 1/00045* (2013.01); *A61B 1/04* (2013.01); *A61B 1/06* (2013.01); *A61B 1/0638* (2013.01); *G02B 23/2461* (2013.01); *H04N 5/2256* (2013.01); *H04N 5/2354* (2013.01); *H04N 5/347* (2013.01); *H04N 5/378* (2013.01); *H04N 9/045* (2013.01); *H04N 9/07* (2013.01); *H04N 2005/2255* (2013.01)

(58) Field of Classification Search
CPC ...... A61B 1/00009; H04N 9/045; H04N 9/07; H04N 5/378
USPC ......................................................... 348/45
See application file for complete search history.

(56) References Cited

U.S. PATENT DOCUMENTS

| | | | |
|---|---|---|---|
| 8,154,613 B2* | 4/2012 | Ikeda | H04N 9/643 348/222.1 |
| 2002/0113195 A1* | 8/2002 | Osada | G06T 3/4007 250/208.1 |
| 2006/0066739 A1* | 3/2006 | Kobayashi | H04N 5/335 348/294 |
| 2011/0184236 A1 | 7/2011 | Yoshino | |

FOREIGN PATENT DOCUMENTS

| | | |
|---|---|---|
| JP | 2011-050676 A | 3/2011 |
| JP | 2011-147707 A | 8/2011 |
| JP | 2012-045265 A | 3/2012 |
| JP | 2012-125331 A | 7/2012 |
| JP | 2012-235281 A | 11/2012 |
| JP | 2014-068894 A | 4/2014 |

* cited by examiner

IMAGE PICKUP SYSTEM

CROSS REFERENCE TO RELATED APPLICATION

This application is a continuation application of PCT/JP2015/075082 filed on Sep. 3, 2015 and claims benefit of Japanese Application No. 2014-205855 filed in Japan on Oct. 6, 2014, the entire contents of which are incorporated herein by this reference.

BACKGROUND OF THE INVENTION

1. Field of the Invention

The present invention relates to an image pickup system, and in particular to an image pickup system for picking up images of light from an object to acquire an image.

2. Description of the Related Art

As a technique for securing an adequate S/N of an image obtained by performing image pickup of weak light from an object by an image pickup device, for example, a technique has been conventionally known in which signals corresponding to a plurality of pixels generated accompanying image pickup of the object by the image pickup device are added and treated as a signal corresponding to one pixel.

More specifically, for example, Japanese Patent Application Laid-Open Publication No. 2011-50676 discloses an ophthalmological photographing apparatus configured to be able to switch between a normal mode for outputting electric charges accumulated in respective pixels of an image pickup device as photoelectric conversion signals one by one and a binning mode for outputting electric charges accumulated in adjoining pixels among the respective pixels of the image pickup device as a bundle of photoelectric conversion signals. Further, Japanese Patent Application Laid-Open Publication No. 2011-50676 also discloses a switching operation of setting the binning mode at time of observing fluorescence from a fundus and setting the normal mode at time of photographing the fluorescence.

On the other hand, for example, in endoscopic observation, a situation of identifying an object such as a lesion existing in a body cavity of a subject in a distant view and a situation of confirming a detailed state of the identified object in a near view may occur. Therefore, in endoscopic observation, it is desirable, for example, that an image with brightness suitable for screening of the lesion in the body cavity is acquired in the distant view, and an image with a resolving power suitable for confirmation of a detailed structure of the lesion is acquired in the near view.

SUMMARY OF THE INVENTION

An image pickup system of an aspect of the present invention is an image pickup system including: a light source apparatus configured to sequentially emit lights with a plurality of mutually different wavelength bands as illumination light for illuminating an object; an objective optical system configured to form an image of light from the object illuminated by the illumination light; an image pickup device provided with an image pickup surface formed by two-dimensionally arranging a plurality of pixels for receiving the light formed by the objective optical system and photoelectrically converting the received light to generate electric signals; a judging portion configured to perform a judgment process for judging: the object is observed in which of a distant view and a near view; and an image pickup control portion configured to perform control for setting a reading mode of the image pickup device to either a single pixel reading mode which is a mode for sequentially reading the electric signals generated by the respective pixels arranged on the image pickup surface one by one, or a pixel addition reading mode which is a mode for, with electric signals generated by one pixel group constituted by a plurality of pixels arranged mutually adjoining one another on the image pickup surface as electric signals corresponding to one pixel, sequentially reading the electric signals corresponding to one pixel, according to a judgment result obtained by the judgment process of the judging portion; wherein the light source apparatus is configured to be able to sequentially emit light of a red wavelength band, light of a green wavelength band and light of a blue wavelength band as the illumination light; and the image pickup control portion performs control for setting the reading mode of the image pickup device to the single pixel reading mode when a judgment result that the object is observed in the distant view is obtained, and it is detected that the light of the blue wavelength band is emitted from the light source apparatus as the illumination light; and performs control for setting the reading mode of the image pickup device to the pixel addition reading mode when the judgment result that the object is observed in the distant view is obtained, and it is detected that the light of the red wavelength band is emitted from the light source apparatus as the illumination light.

An image pickup system of an aspect of the present invention is an image pickup system including: a light source apparatus configured to sequentially emit lights with a plurality of mutually different wavelength bands as illumination light for illuminating an object; an objective optical system configured to form an image of light from the object illuminated by the illumination light; an image pickup device provided with an image pickup surface formed by two-dimensionally arranging a plurality of pixels for receiving the light formed by the objective optical system and photoelectrically converting the received light to generate electric signals; a judging portion configured to perform a judgment process for judging: the object is observed in which of a distant view and a near view; and an image pickup control portion configured to perform control for setting a reading mode of the image pickup device to either a single pixel reading mode which is a mode for sequentially reading the electric signals generated by the respective pixels arranged on the image pickup surface one by one, or a pixel addition reading mode which is a mode for, with electric signals generated by one pixel group constituted by a plurality of pixels arranged mutually adjoining one another on the image pickup surface as electric signals corresponding to one pixel, sequentially reading the electric signals corresponding to one pixel, according to a judgment result obtained by the judgment process of the judging portion; wherein the light source apparatus is configured to be able to sequentially emit light of a red wavelength band, light of a green wavelength band and light of a blue wavelength band as the illumination light; and the image pickup control portion performs control for setting the reading mode of the image pickup device to the single pixel reading mode when a judgment result that the object is observed in the distant view is obtained, and it is detected that the light of the green wavelength band or the light of the blue wavelength band is emitted from the light source apparatus as the illumination light; and performs control for setting the reading mode of the image pickup device to the pixel addition reading mode when the judgment result that the object is observed in the distant view is obtained, and it is detected that the light of the red wavelength band is emitted from the light source apparatus as the illumination light.

DETAILED DESCRIPTION OF THE PREFERRED EMBODIMENTS

Embodiments of the present invention will be described with reference to drawings.

First Embodiment

FIGS. 1 to 5 relate to a first embodiment of the present invention.

Figure 1:
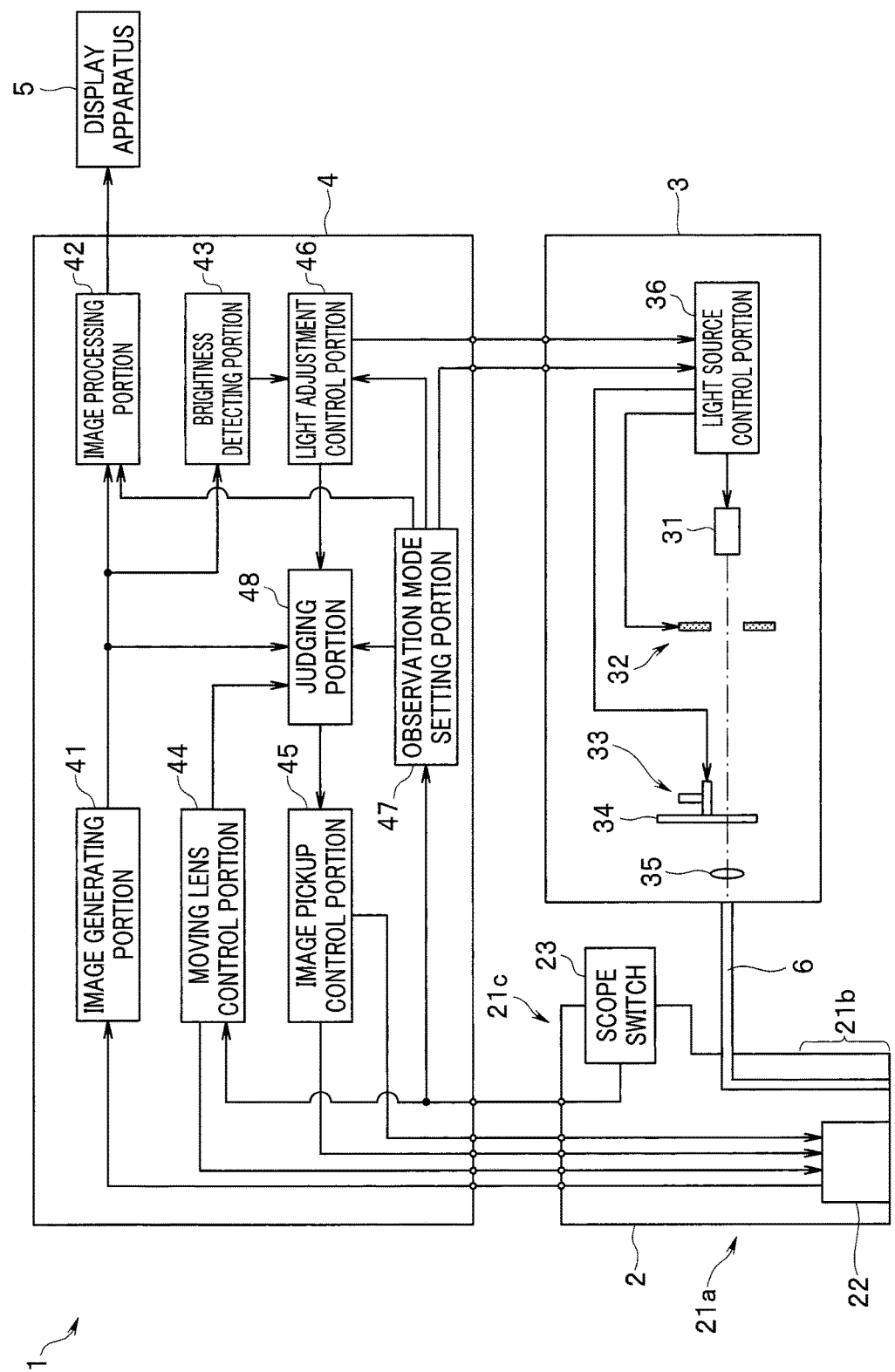
FIG. 1 is a diagram showing a configuration of a main part of an image pickup system according to a first embodiment.

As shown in FIG. 1, an image pickup system 1 is configured having an endoscope 2, a light source apparatus 3, a processor 4 and a display apparatus 5. FIG. 1 is a diagram showing the configuration of a main part of the image pickup system according to the first embodiment.

As shown in FIG. 1, the endoscope 2 is configured having an insertion portion 21a with a shape and dimensions insertable into a body cavity of a subject, a distal end portion 21b provided on a distal end side of the insertion portion 21a, and an operation portion 21c provided on a proximal end side of the insertion portion 21a. Further, inside the insertion portion 21a, a light guide 6 for transmitting illumination light emitted from the light source apparatus 3 to the distal end portion 21b is inserted.

An incident end face of the light guide 6 is detachably connected to the light source apparatus 3 via an optical connector or the like not shown. Further, an emission end face of the light guide 6 is arranged in a vicinity of an illumination optical system not shown, which is provided on the distal end portion 21b of the endoscope 2. According to such a configuration, the illumination light emitted from the light source apparatus 3 is emitted to the subject via the light guide 6 connected to the light source apparatus 3 and the illumination optical system not shown, which is provided on the distal end portion 21b.

The distal end portion 21b of the endoscope 2 is provided with an image pickup unit 22 configured to pick up images of light (return light) from an object illuminated by the illumination light emitted via the light guide 6, generate image pickup signals corresponding to the picked-up light (return light) and output the generated image pickup signals to the processor 4.

Figure 2:
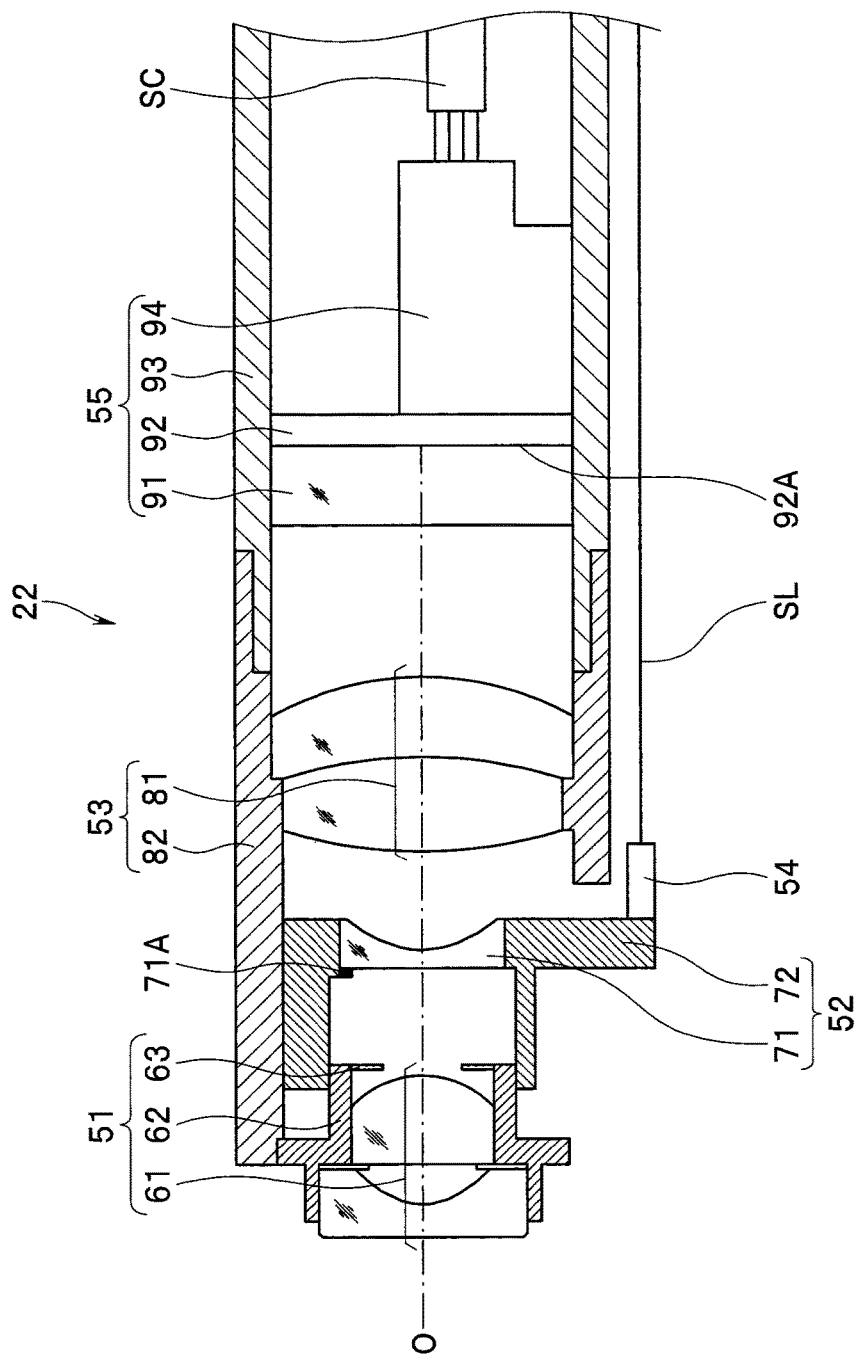
FIG. 2 is a diagram showing a schematic configuration of an image pickup unit.

As shown in FIG. 2, the image pickup unit 22 is configured to form an image of the light (return light) from the object by an objective optical system provided with a front lens group unit 51, a moving lens unit 52 and a rear lens group unit 53. Further, as shown in FIG. 2, the image pickup unit 22 is configured having an actuator 54 configured to generate driving force for causing the moving lens unit 52 to move, and an image sensor unit 55 provided with an image pickup device 92 for picking up images of the light formed by the objective optical system described above. FIG. 2 is a diagram showing a schematic configuration of the image pickup unit.

The front lens group unit 51 is configured having a front lens group 61 provided with a plurality of lenses onto which the light (return light) from the object is incident, a front lens group frame 62 for holding the front lens group 61, and an objective aperture 63 provided at a most rear end of the front lens group frame 62.

The objective aperture 63 is configured to be connected to an image pickup control portion 45 (to be described later) of the processor 4 via a signal line not shown. Further, the objective aperture 63 is configured to be able to adjust an aperture amount so that the front lens group unit 51 is provided with an F value suitable for a pseudo change in a pixel pitch accompanying a reading mode of the image pickup device 92 (to be described later) being changed, based on control of the image pickup control portion 45 of the processor 4.

The moving lens unit 52 is configured having a moving lens 71 configured so that light which has passed through the front lens group unit 51 is incident and formed being provided with an optical indicator 71A on an outer edge portion of a light incident surface, and a moving lens frame 72 formed so as to be able to slide along a direction of an optical axis O of the objective optical system of the image pickup unit 22 while holding the moving lens 71.

The optical indicator 71A is formed, for example, by vapor-depositing light blocking material at a predetermined position on the outer edge portion of the light incident surface of the moving lens 71. Further, the optical indicator 71A is provided, for example, at a position of not being picked up by the image pickup device 92 (to be described later) of the image sensor unit 55 when the moving lens 71 is arranged at a predetermined arrangement position TP or on a front side of the predetermined arrangement position TP, and at a position of being picked up by the image pickup device 92 of the image sensor unit 55 when the moving lens 71 is arranged on a rear side of the predetermined arrangement position TP.

The rear lens group unit 53 is configured having a rear lens group 81 provided with a plurality of lenses onto which the light which has passed through the moving lens unit 52 is incident, and a rear lens group frame 82 for holding the rear lens group 81.

The actuator 54 is configured to be connected to a moving lens control portion 44 (to be described later) of the processor 4 via a signal line SL. Further, the actuator 54 is configured to, according to control of the moving lens control portion 44 of the processor 4, generate driving force for causing the moving lens unit 52 to slide along the direction of the optical axis O of the objective optical system of the image pickup unit 22 and supply the generated driving force to the moving lens frame 72.

The image sensor unit 55 is connected to each of an image generating portion 41 (to be described later) and an image pickup control portion 45 (to be described later) of the processor 4 via a signal cable SC including a plurality of signal lines. Further, the image sensor unit 55 is configured to generate image pickup signals by picking up images of light incident via the rear lens group unit 53 and output the generated image pickup signals to the image generating portion 41 of the processor 4. Further, the image sensor unit 55 is configured having cover glass 91 on which the light which has passed through the rear lens group unit 53 is incident, the image pickup device 92 configured to receive the light which has passed through the cover glass 91 and generate an electric signal by photoelectrically converting the received light, a holding frame 93 for holding the cover glass 91 and the image pickup device 92, and a circuit substrate 94 electrically connected to the image pickup device 92.

The image pickup device 92 is, for example, provided with an image pickup surface 92A which is formed by two-dimensionally arranging pixels and includes a CMOS sensor, and configured to perform an operation corresponding to control of the image pickup control portion 45.

Figure 3:
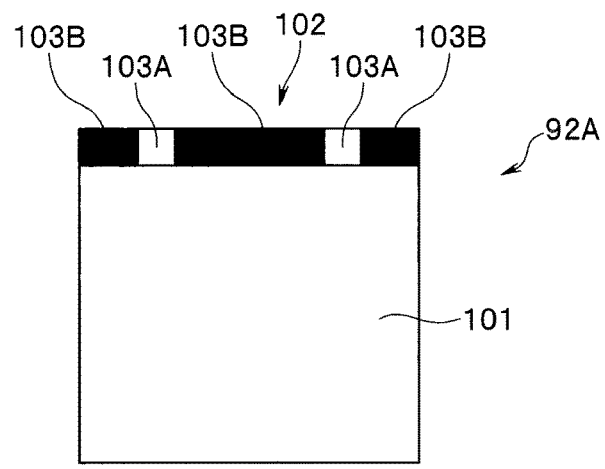
FIG. 3 is a diagram showing a schematic configuration of an image pickup surface of an image pickup device provided in the image pickup unit.

For example, as shown in FIG. 3, the image pickup surface 92A is configured having a light receiving portion 101 and a light blocking portion 102. FIG. 3 is a diagram showing a schematic configuration of the image pickup surface of the image pickup device provided in the image pickup unit.

The light receiving portion 101 is provided with a function as an effective pixel area and is formed by two-dimensionally arranging a plurality of pixels for receiving the light which has passed the cover glass 91 and photoelectrically converting the received light to generate electric signals. Further, the light receiving portion 101 is configured to be able to perform an operation corresponding to a single pixel reading mode which is a mode for sequentially reading the electric signals generated by the respective pixels one by one, or a pixel addition reading mode which is a mode for, with electric signals generated by one pixel group constituted by a plurality of pixels arranged mutually adjoining one another as electric signals corresponding to one pixel, sequentially reading electric signals of pixel groups, according to control of the image pickup control portion 45.

The light blocking portion 102 is formed to cover a part of pixels arranged on an outer edge portion of the image pickup surface 92A. Further, the light blocking portion 102 is configured having openings 103A formed so as to cause light which has passed through the cover glass 91 to pass through and light blocking members 103B formed so as to block the light which has passed through the cover glass 91. That is, according to such a configuration of the light blocking portion 102, light which has passed through the cover glass 91 is received, and electric signals corresponding to the received light are generated, by pixels or pixel groups arranged at a position of the openings 103A.

The circuit substrate 94 is configured being provided, for example, with a signal processing circuit or the like. Further, the circuit substrate 94 is configured, for example, to generate image pickup signals by performing predetermined processing for the electric signals outputted from the image pickup device 92 and output the generated image pickup signals to the signal cable SC.

The operation portion 21c of the endoscope 2 is provided with a scope switch 23 provided with a plurality of switches capable of giving an instruction corresponding to a user operation to the processor 4.

More specifically, the scope switch 23 is configured being provided, for example, with switches such as a lens driving switch capable of giving in instruction to cause the moving lens unit 52 to move forward or backward along the direction of the optical axis O of the objective optical system of the image pickup unit 22 and an observation mode setting switch capable of giving an instruction to set an observation mode of the image pickup system 1 to either a white light observation mode or a special light observation mode.

As shown in FIG. 1, the light source apparatus 3 is configured having a white light source 31, a light source aperture 32, a filter driving mechanism 33, a rotating filter 34, a light condensing optical system 35 and a light source control portion 36.

The white light source 31 is provided, for example, with a xenon lamp, a white LED or the like and configured to be switched on or off according to control of the light source control portion 36. Further, the white light source 31 is configured to be able to emit an amount of white light corresponding to a magnitude of a driving current supplied from the light source control portion 36. That is, according to the present embodiment, it is possible to adjust a light amount of illumination light emitted from the light source apparatus 3 to a light amount corresponding to the magnitude of the driving current supplied to the white light source 31. Note that, according to the present embodiment, for example, when the white light source 31 is configured being provided with a white LED, the light amount of the illumination light emitted from the light source apparatus 3 may be adjusted by performing PWM (pulse width modulation) control which is control of the light source control portion 36 causing a ratio of a lighting time period to an extinction time period of the white LED within a predetermined unit time period to change.

The light source aperture 32 is, for example, arranged on an emission optical path of the white light source 31 and configured to be able to, by causing an aperture amount to change according to control of the light source control portion 36, adjust a light amount of white light incident on the rotating filter 34 via the emission optical path to a light amount corresponding to the aperture amount. That is, according to the present embodiment, it is possible to adjust the light amount of the illumination light emitted from the light source apparatus 3 to a light amount corresponding to the aperture amount of the light source aperture 32.

More specifically, the light source aperture 32 is provided, for example, with a configuration similar to the configuration of an electric aperture device disclosed in Japanese Patent Application Laid-Open Publication No. 2006-184459.

The filter driving mechanism 33 is configured to generate driving force according to control of the light source control portion 36 and supply the generated driving force to the rotating filter 34.

More specifically, the filter driving mechanism 33 is configured being provided, for example, with a first motor configured to generate driving force for causing the rotating filter 34 to rotate, a second motor configured to generate driving force for causing the rotating filter 34 to move along a direction vertical to the emission optical path of the white light source 31, and gear mechanisms for transmitting the driving forces generated by the first motor and the second motor, respectively.

Figure 4:
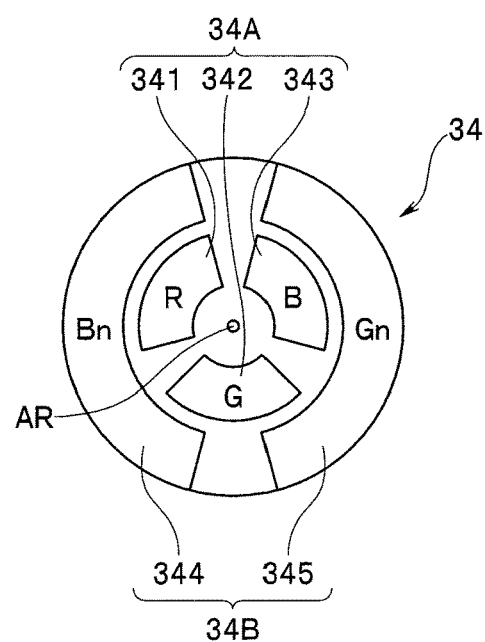
FIG. 4 is a diagram showing an example of a configuration of a rotating filter.

The rotating filter 34 is formed, for example, having a disk shape as shown in FIG. 4 and configured to rotate with a rotation axis AR as a center, according to the driving force generated in the filter driving mechanism 33. Further, the rotating filter 34 has, for example, a first filter group 34A provided with a plurality filters provided along a circumferential direction on an inner circumference side and a second filter group 34B provided with a plurality filters provided along the circumferential direction on an outer circumferential side as shown in FIG. 4. Note that, in the rotating filter 34, a part other than a part where each filter of the first filter group 34A and the second filter group 34B is arranged is assumed to be configured with a light blocking member. FIG. 4 is a diagram showing an example of a configuration of the rotating filter.

The first filter group 34A is configured having an R filter 341 configured to cause red broadband light (hereinafter referred to as R light) to be transmitted, a G filter 342 configured to cause green broadband light (hereinafter referred to as G light) to be transmitted and a B filter 343 configured to cause blue broadband light (hereinafter referred to as B light) to be transmitted. Further, the first filter group 34A is formed so that an area ratio of the R filter 341, the G filter 342 and the B filter 343 becomes 1:1:1.

More specifically, the R filter 341 is formed being provided, for example, with such an optical characteristic that causes light of a wavelength band from 600 nm to 700 nm to be transmitted. Further, the G filter 342 is formed being provided, for example, with such an optical characteristic that causes light of a wavelength band from 500 nm to 600 nm to be transmitted. Further, the B filter 343 is formed being provided, for example, with such an optical characteristic that causes light of a wavelength band from 400 nm to 500 nm to be transmitted.

The second filter group 34B is configured having a Bn filter 344 configured to cause blue narrowband light (hereinafter referred to as Bn light) to be transmitted and a Gn filter 345 configured to cause only green narrowband light (hereinafter referred to as Gn light) to be transmitted.

More specifically, the Bn filter 344 is formed being provided, for example, with such an optical characteristic that causes light of a wavelength band from 400 nm to 430 nm to be transmitted. Further, the Gn filter 345 is formed being provided, for example, with such an optical characteristic that causes light of a wavelength band from 530 nm to 550 nm to be transmitted.

The light condensing optical system 35 is provided, for example, with an optical member such as a lens and configured to condense light which has passed through the rotating filter 34 and emit the light to the incident end face of the light guide 6.

The light source control portion 36 is configured to be able to cause the aperture amount of the light source aperture 32 to change, according to control of a light adjustment control portion 46 of the processor 4. Further, the light source control portion 36 is configured to be able to cause rotation speed of the rotating filter 34 to change by controlling the filter driving mechanism 33 according to control of the light adjustment control portion 46 of the processor 4. Further, the light source control portion 36 is configured to be able to supply a driving current for driving the white light source 31 and able to cause a magnitude of the driving current (a current value) to change according to control of the light adjustment control portion 46 of the processor 4.

The light source control portion 36 is configured to, for example, when the observation mode of the image pickup system 1 is set to the white light observation mode, cause the first filter group 34A to be arranged on the emission optical path of the white light source 31 and cause the second filter group 34B to be withdrawn from the emission optical path by controlling the filter driving mechanism 33 according to control of an observation mode setting portion 47 (to be described later) of the processor 4. Further, the light source control portion 36 is configured to, for example, when the observation mode of the image pickup system 1 is set to the special light observation mode, cause the second filter group 34B to be arranged on the emission optical path of the white light source 31 and cause the first filter group 34A to be withdrawn from the emission optical path by controlling the filter driving mechanism 33 according to control of the observation mode setting portion 47 of the processor 4.

That is, according to the configuration as described above, when the observation mode of the image pickup system 1 is set to the white light observation mode, R light, G light and B light are generated by white light emitted from the white light source 31 passing through the first filter group 34A, and the generated R light, G light and B light are sequentially emitted from the light source apparatus 3 as illumination light. Further, according to the configuration as described above, when the observation mode of the image pickup system 1 is set to the special light observation mode, Bn light and Gn light are generated by white light emitted from the white light source 31 passing through the second filter group 34B, and the generated Bn light and Gn light are sequentially emitted from the light source apparatus 3 as illumination light.

As shown in FIG. 1, the processor 4 is configured having the image generating portion 41, an image processing portion 42, a brightness detecting portion 43, the moving lens control portion 44, the image pickup control portion 45, the light adjustment control portion 46, the observation mode setting portion 47 and a judging portion 48.

The image generating portion 41 is configured being provided, for example, with a noise removal circuit and an A/D conversion circuit. Further, the image generating portion 41 is configured to generate images by performing predetermined signal processing for the image pickup signals emitted from the endoscope 2, and output the generated images to the image processing portion 42, the brightness detecting portion 43 and the judging portion 48.

The image processing portion 42 is configured being provided, for example, with an image processing circuit and a synchronization circuit.

Further, the image processing portion 42 is configured to, by performing predetermined image processing such as masking and synchronization for the images outputted from the image generating portion 41, generate an observation image in which outer edge portions of the images are set as an invisible area, and output the generated observation image to the display apparatus 5. That is, according to such image processing, for example, even when images including the optical indicator 71A are outputted from the image generating portion 41, it is possible to display an observation image not including the optical indicator 71A on the display apparatus 5. Further, according to the image processing as described above, it is also possible to display, for example, an observation image not including the openings 103A of the light blocking portion 102 on the display apparatus 5.

The image processing portion 42 is configured to, for example, when the observation mode of the image pickup system 1 is set to the white color observation mode, generate an RGB color image corresponding to an image RI obtained by picking up an image of return light of R light, an image GI obtained by picking up an image of return light of G light and an image BI obtained by picking up an image of return light of B light, which are the images outputted from the image generating portion 41, as an observation image according to control of the observation mode setting portion 47. Further, the image processing portion 42 is configured to, for example, when the observation mode of the image pickup system 1 is set to the special color observation mode, generate a pseudo color image corresponding to an image BnI obtained by picking up an image of return light of Bn light and an image GnI obtained by picking up an image of return light of Gn light, which are the images outputted from the image generating portion 41, as an observation image according to control of the observation mode setting portion 47.

The brightness detecting portion 43 is configured to detect brightness of the images outputted from the image generating portion 41 and output brightness information, which is information indicating the detected brightness, to the light adjustment control portion 46.

More specifically, the brightness detecting portion 43 is configured, for example, to calculate an average value of luminance values in the images outputted from the image generating portion 41 and output the calculated average value of the luminance values to the light adjustment control portion 46 as the brightness information.

The moving lens control portion 44 is configured to perform control for causing the moving lens unit 52 to move according to an instruction given by the lens driving switch of the scope switch 23. Further, the moving lens control portion 44 is configured, for example, to identify a current position of the moving lens 71 in the image pickup unit 22 based on a movement state of the moving lens unit 52 and output lens position information showing the identified current position of the moving lens 71 to the judging portion 48.

The image pickup control portion 45 is configured to perform control for setting the reading mode of the light receiving portion 101 of the image pickup device 92 to either the single pixel reading mode or the pixel addition reading mode, according to a judgment result obtained by a judgment process (to be described later) of the judging portion 48.

The image pickup control portion 45 is configured to perform control for causing an exposure time period of the light receiving portion 101 of the image pickup device 92 to change, according to a judgment result obtained by the judgment process (to be described later) of the judging portion 48.

The image pickup control portion 45 is configured to perform control for causing the aperture amount of the objective aperture 63 to change as control for causing the F value of the front lens group unit 51 to change, according to a judgment result obtained by the judgment process (to be described later) of the judging portion 48.

The light adjustment control portion 46 is configured to perform control for causing each of the aperture amount of the light source aperture 32 and the magnitude of the driving current supplied to the white light source 31 to change while keeping the rotation speed of the rotating filter 34 constant so that brightness shown by the brightness information outputted from the brightness detecting portion 43 becomes brightness suitable for a current observation mode, and output aperture amount information indicating a current aperture amount of the light source aperture 32 and driving current information showing a magnitude of a driving current currently supplied to the white light source 31 to the judging portion 48, according to control of the observation mode setting portion 47.

More specifically, for example, when the observation mode of the image pickup system 1 is set to the white light observation mode, the light adjustment control portion 46 performs control for causing each of the aperture amount of the light source aperture 32 and the magnitude of the driving current supplied to the white light source 31 to change so that the brightness shown by the brightness information outputted from the brightness detecting portion 43 becomes a brightness target value WT in the white light observation mode, according to control of the observation mode setting portion 47. That is, according to such control of the light adjustment control portion 46, for example, when the brightness shown by the brightness information outputted from the brightness detecting portion 43 is below the brightness target value WT in the white light observation mode, brightness of the images outputted from the image generating portion 41 increases as the aperture amount of the light source aperture 32 is decreased and/or the magnitude of the driving current supplied to the white light source 31 is increased. Further, according the control of the light adjustment control portion 46 as described above, for example, when the brightness shown by the brightness information outputted from the brightness detecting portion 43 is equal to or above the brightness target value WT in the white light observation mode, the brightness of the images outputted from the image generating portion 41 decreases as the aperture amount of the light source aperture 32 is increased and/or the magnitude of the driving current supplied to the white light source 31 is decreased.

On the other hand, for example, when the observation mode of the image pickup system 1 is set to the special light observation mode, the light adjustment control portion 46 performs control for causing each of the aperture amount of the light source aperture 32 and the magnitude of the driving current supplied to the white light source 31 to change so that the brightness shown by the brightness information outputted from the brightness detecting portion 43 becomes a brightness target value ST in the special light observation mode, according to control of the observation mode setting portion 47. That is, according to such control of the light adjustment control portion 46, for example, when the brightness shown by the brightness information outputted from the brightness detecting portion 43 is below the brightness target value ST in the special light observation mode, brightness of the images outputted from the image generating portion 41 increases as the aperture amount of the light source aperture 32 is decreased and/or the magnitude of the driving current supplied to the white light source 31 is increased. Further, according the control of the light adjustment control portion 46 as described above, for example, when the brightness shown by the brightness information outputted from the brightness detecting portion 43 is equal to or above the brightness target value ST in the special light observation mode, the brightness of the images outputted from the image generating portion 41 decreases as the aperture amount of the light source aperture 32 is increased and/or the magnitude of the driving current supplied to the white light source 31 is decreased.

Note that the light adjustment control portion 46 of the present embodiment may not necessarily perform control as described above, but may be configured, for example, to perform control for causing the rotation speed of the rotating filter 34 to change while keeping the aperture amount of the light source aperture 32 constant so that the brightness shown by the brightness information outputted from the brightness detecting portion 43 becomes brightness suitable for a current observation mode, and output rotation speed information showing current rotation speed of the rotating filter 34 to the judging portion 48, according to control of the observation mode setting portion 47.

More specifically, for example, when the observation mode of the image pickup system 1 is set to the white light observation mode, the light adjustment control portion 46 performs control for causing the rotation speed of the rotating filter 34 to change so that the brightness shown by the brightness information outputted from the brightness detecting portion 43 becomes the brightness target value WT in the white light observation mode, according to control of the observation mode setting portion 47. That is, according to such control of the light adjustment control portion 46, for example, when the brightness shown by the brightness information outputted from the brightness detecting portion 43 is below the brightness target value WT in the white light observation mode, the rotation speed of the rotating filter 34 is decreased. Further, according to the control of the light adjustment control portion 46 as described above, for example, when the brightness shown by the brightness information outputted from the brightness detecting portion 43 is equal to or above the brightness target value WT in the white light observation mode, the rotation speed of the rotating filter 34 is increased.

On the other hand, for example, when the observation mode of the image pickup system 1 is set to the special light observation mode, the light adjustment control portion 46 performs control for causing the rotation speed of the rotating filter 34 to change so that the brightness shown by the brightness information outputted from the brightness detecting portion 43 becomes the brightness target value ST in the special light observation mode, according to control of the observation mode setting portion 47. That is, according to such control of the light adjustment control portion 46, for example, when the brightness shown by the brightness information outputted from the brightness detecting portion 43 is below the brightness target value ST in the special light observation mode, the rotation speed of the rotating filter 34 is decreased. Further, according to the control of the light adjustment control portion 46 as described above, for example, when the brightness shown by the brightness information outputted from the brightness detecting portion 43 is equal to or above the brightness target value ST in the special light observation mode, the rotation speed of the rotating filter 34 is increased.

That is, the light adjustment control portion 46 of the present embodiment is configured to perform control for adjusting the light amount of the illumination light emitted from the light source apparatus 3 so that the brightness shown by the brightness information outputted from the brightness detecting portion 43 becomes brightness suitable for a current observation mode, and output at least the aperture amount information and the driving current information to the judging portion 48 as control information showing a current control state in the adjustment of the light amount of the illumination light.

The observation mode setting portion 47 is configured to detect a current observation mode set by a lens observation mode setting switch of the scope switch 23 and perform control for causing the light source control portion 36, the image processing portion 42 and the light adjustment control portion 46 to perform operations corresponding to the detected current observation mode. Further, the observation mode setting portion 47 is configured to detect the current observation mode set by the lens observation mode setting switch of the scope switch 23 and output observation mode information showing the detected current observation mode to the judging portion 48.

The judging portion 48 is configured to perform a judgment process for judging: the object is observed in which of a distant view and a near view, based on any of the following: the images outputted from the image generating portion 41, the lens position information outputted from the moving lens control portion 44, the aperture amount infor- mation outputted from the light adjustment control portion 46, the driving current information outputted from the light adjustment control portion 46, the rotation speed information outputted from the light adjustment control portion 46 and the observation mode information outputted from the observation mode setting portion 47. Further, the judging portion 48 is configured to output a judgment result obtained by the judgment process described above to the image pickup control portion 45.

The display apparatus 5 is provided, for example, with a monitor and the like and configured to be able to display the observation image outputted from the processor 4.

Next, operation of the image pickup system 1 provided with the configuration as described above will be described.

After powering on each portion of the image pickup system 1, a user such as a surgeon arranges the distal end portion 21b at a position where it is possible to pick up images of a desired object in a body cavity of a subject and performs observation of the desired object in a state that a desired observation mode is set, by inserting the insertion portion 21a into the body cavity of the subject while confirming an image displayed on the display apparatus 5. Then, in response to such a user operation, illumination light corresponding to the desired observation mode is sequen- tially radiated to the desired object from the distal end portion 21b; image pickup signals are generated by picking up images of return light from the desired object illuminated by the illumination light; the generated image pickup signals are outputted to the image generating portion 41 from the image pickup unit 22; and images generated by performing predetermined signal processing for the image pickup sig- nals are outputted from the image generating portion 41 to the image processing portion 42, the brightness detecting portion 43 and the judging portion 48.

The judging portion 48 performs the judgment process for judging: the object is observed in which of the distant view and the near view, based on any of the following: the images outputted from the image generating portion 41, the lens position information outputted from the moving lens control portion 44, the aperture amount information outputted from the light adjustment control portion 46, the driving current information outputted from the light adjustment control portion 46, the rotation speed information outputted from the light adjustment control portion 46 and the observation mode information outputted from the observation mode setting portion 47.

Here, a specific example of the judgment process per- formed by the judging portion 48 of the present embodiment will be described below. Note that the judging portion 48 of the present embodiment is assumed to perform one process determined in advance among respective processes enumer- ated below, as the judgment process described above.

The judging portion 48 detects whether or not luminance values of pixels or pixel groups involved in image pickup of light which has passed the openings 103A of the light blocking portion 102, among respective pixels included in the images outputted from the image generating portion 41, is equal to or above a threshold TH1. When detecting that the luminance value of the pixels or the pixel groups involved in the image pickup of the light which has passed the openings 103A of the light blocking portion 102 is below the threshold TH1, the judging portion 48 obtains a judg- ment result that the object is observed in the distant view. Further, when detecting that the luminance value of the pixels or the image groups involved in the image pickup of the light which has passed the openings 103A of the light blocking portion 102 is equal to or above the threshold TH1, the judging portion 48 obtains a judgment result that the object is observed in the near view.

The judging portion 48 detects whether or not the optical indicator 71A is included in the images outputted from the image generating portion 41. Then, when detecting that the optical indicator 71A is included in the images outputted from the image generating portion 41, the judging portion 48 obtains the judgment result that the object is observed in the distant view. Further, when detecting that the optical indicator 71A is not included in the images outputted from the image generating portion 41, the judging portion 48 obtains the judgment result that the object is observed in the near view.

The judging portion 48 detects whether or not a current arrangement position of the moving lens 71 in the image pickup unit 22 is on a rear side of a predetermined position TQ, based on the lens position information outputted from the moving lens control portion 44. Then, when detecting that the current arrangement position of the moving lens 71 in the image pickup unit 22 is on the rear side of the predetermined position TQ, the judging portion 48 obtains the judgment result that the object is observed in the distant view. Further, when detecting that the current arrangement position of the moving lens 71 in the image pickup unit 22 is at the predetermined position TQ or on a front side of the predetermined position TQ, the judging portion 48 obtains the judgment result that the object is observed in the near view.

Note that, in the present embodiment, it is only required to obtain a judgment result corresponding to farness or nearness in terms of optical depth. Therefore, in the present embodiment, a judgment process different from the judgment process described above may be performed depending on optical characteristics of each lens unit of the image pickup unit 22. More specifically, the judging portion 48 of the present embodiment may, for example, obtain the judgment result that the object is observed in the near view when detecting that the current arrangement position of the moving lens 71 is on the rear side of the predetermined position TQ, and obtain the judgment result that the object is observed in the distant view when detecting that the current arrangement position of the moving lens 71 is the position TQ or on the front side of the predetermined position TQ.

The judging portion 48 detects whether or not a current aperture amount of the light source aperture 32 is equal to or above a threshold TH2, based on the aperture amount information outputted from the light adjustment control portion 46. Then, when detecting that the current aperture amount of the light source aperture 32 is equal to or above the threshold TH2, the judging portion 48 obtains the judgment result that the object is observed in the distant view. Further, when detecting that the current aperture amount of the light source aperture 32 is below the threshold TH2, the judging portion 48 obtains the judgment result that the object is observed in the near view.

The judging portion 48 detects whether or not a magnitude of a driving current currently supplied to the white light source 31 is equal to or above a threshold TH3, based on the driving current information outputted from the light adjustment control portion 46. Then, when detecting that the magnitude of the driving current currently supplied to the white light source 31 is equal to or above the threshold TH3, the judging portion 48 obtains the judgment result that the object is observed in the distant view. Further, when detecting that the magnitude of the driving current currently supplied to the white light source 31 is below the threshold TH3, the judging portion 48 obtains the judgment result that the object is observed in the near view.

The judging portion 48 detects whether or not current rotation speed of the rotating filter 34 is below a threshold TH4, based on the rotation speed information outputted from the light adjustment control portion 46. Then, when detecting that the current rotation speed of the rotating filter 34 is below the threshold TH4, the judging portion 48 obtains the judgment result that the object is observed in the distant view. Further, when detecting that the current rotation speed of the rotating filter 34 is equal to or above the threshold TH4, the judging portion 48 obtains the judgment result that the object is observed in the near view.

The judging portion 48 detects which of the white light observation mode and the special light observation mode a current observation mode is, based on the observation mode information outputted from the observation mode setting portion 47. Then, when detecting that the current observation mode is the special light observation mode, the judging portion 48 obtains the judgment result that the object is observed in the near view. That is, when detecting that a narrowband light is emitted from the light source apparatus 3 as illumination light for illuminating the object, based on the observation mode information outputted from the observation mode setting portion 47, the judging portion 48 obtains the judgment result that the object is observed in the near view.

Note that it is assumed that, when detecting that the current observation mode is the white light observation mode, the judging portion 48 judges: the object is observed in which of the distant view and the near view, by performing the judgment process based on any of the following: the images outputted from the image generating portion 41, the lens position information outputted from the moving lens control portion 44, the aperture amount information outputted from the light adjustment control portion 46, the driving current information outputted from the light adjustment control portion 46, and the rotation speed information outputted from the light adjustment control portion 46.

When the object is observed in the distant view according to a judgment result obtained by the judgment process of the judging portion 48, the image pickup control portion 45 performs control for causing the aperture amount of the objective aperture 63 to increase up to a predetermined aperture amount SA (closing the objective aperture 63) as control for increasing the F value of the front lens group unit 51. Further, when the object is observed in the near view according to a judgment result obtained by the judgment process of the judging portion 48, the image pickup control portion 45 performs control for causing the aperture amount of the objective aperture 63 to decrease down to a predetermined aperture amount SB (opening the objective aperture 63) as control for decreasing the F value of the front lens group unit 51.

When the object is observed in the distant view according to a judgment result obtained by the judgment process of the judging portion 48, the image pickup control portion 45 performs control for causing the exposure time period of the light receiving portion 101 of the image pickup device 92 to increase up to a predetermined exposure time period EA. Further, when the object is observed in the near view according to a judgment result obtained by the judgment process of the judging portion 48, the image pickup control portion 45 performs control for causing the exposure time period of the light receiving portion 101 of the image pickup device 92 to decrease down to a predetermined exposure time period EB.

When the object is observed in the near view according to a judgment result obtained by the judgment process of the judging portion 48, the image pickup control portion 45 performs control for setting the reading mode of the light receiving portion 101 of the image pickup device 92 to the single pixel reading mode. Further, when the object is observed in the distant view according to a judgment result obtained by the judgment process of the judging portion 48, the image pickup control portion 45 performs control for setting the reading mode of the light receiving portion 101 of the image pickup device 92 to the pixel addition reading mode.

Figure 5:
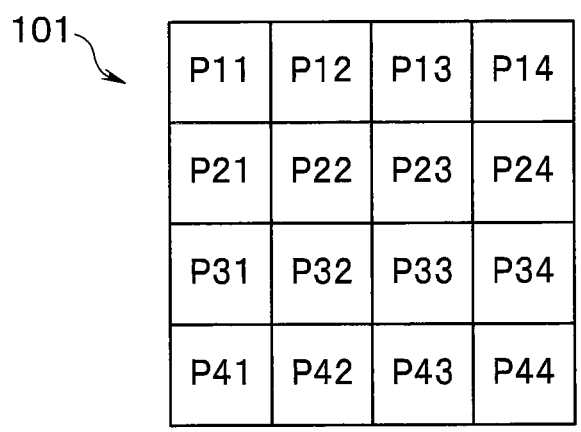
FIG. 5 is a diagram for illustrating a specific example of reading operations performed by a light receiving portion.

Here, specific examples of reading operations in the single pixel reading mode and the pixel addition reading mode set according to control of the image pickup control portion 45 will be described below. Note that, in the description below, a case where the light receiving portion 101 is provided with sixteen pixels P11 to P44 arranged as shown in FIG. 5, that is, a case where the light receiving portion 101 is constituted by 4×4 pixels will be described as an example for simplification. Further, in the present embodiment, reading operations suitable for the number of pixels of the light receiving portion 101 may be caused to be performed, by appropriately modifying the reading operations described below. FIG. 5 is a diagram for illustrating a specific example of the reading operations performed by the light receiving portion 101.

The light receiving portion 101 performs an operation for sequentially reading the electric signals generated by the respective pixels one by one, as the reading operation of the single pixel reading mode, according to control of the image pickup control portion 45.

More specifically, as the reading operation of the single pixel reading mode, the light receiving portion 101 performs, for example, an operation of, after sequentially reading electric signals generated by the respective pixels P11 to P14 on a horizontal line with the pixel P11 arranged on most upper-left as a starting point, one by one, further sequentially reading electric signals generated by the respective pixels P21 to P24 on a horizontal line with the pixel P21 arranged right under the pixel P11 as a starting point, one by one. That is, according to such a reading operation of the single pixel reading mode, reading of electric signals corresponding to one frame is completed at a timing of having read the electric signal generated by the pixel P44.

Further, the light receiving portion 101 performs, for example, an operation for sequentially reading electric signals generated by one pixel group constituted by a plurality of pixels arranged being mutually adjoining one another, as electric signals corresponding to one pixel, as the reading operation of the pixel addition reading mode, according to control of the image pickup control portion 45. It is assumed that, in the pixel addition reading mode set according to the control of the image pickup control portion 45, reading of the electric signals is performed in a state that a part of pixels of mutually adjoining pixel groups are overlapped.

More specifically, as the reading operation of the pixel addition reading mode, the light receiving portion 101 performs, for example, an operation of adding electric signals generated by a pixel group constituted by four pixels P11, P12, P21 and P22 and reading a result as an electric signal corresponding to one pixel, adding electric signals generated by a pixel group constituted by four pixels P12, P13, P22 and P23 and reading a result as an electric signal corresponding to one pixel, adding electric signals generated by a pixel group constituted by four pixels P13, P14, P23 and P24 and reading a result as an electric signal corresponding to one pixel and adding electric signals generated by a pixel group constituted by four pixels P21, P22, P31 and P32 and reading the electric signals as an electric signal corresponding to one pixel. That is, according to such a reading operation of the pixel addition reading mode, reading of electric signals corresponding to one frame is completed at a timing of having added the electric signals generated by a pixel group constituted by the four pixels P33, P34, P43 and P44 and read a result as an electric signal corresponding to one pixel. Further, according to the reading operation of the pixel addition reading mode as described above, since it is possible to reduce the number of times of reading electric signals in comparison with the reading operation of the single pixel reading mode, it is possible to complete reading of electric signals corresponding to one frame at a higher speed than the single pixel reading mode.

As described above, according to the present embodiment, by the reading operation by the pixel addition reading mode being performed when the object is observed in the distance view, it is possible to cause a high S/N observation image with brightness suitable, for example, for identifying the object such as a lesion existing in the body cavity of the subject to be displayed on the display apparatus 5. Further, as described above, according to the present embodiment, by the reading operation by the single pixel reading mode being performed when the object is observed in the near view, it is possible to cause a high-resolution observation image, for example, provided with a resolving power suitable for confirming a detailed state of the object such as a lesion to be displayed on the display apparatus 5.

Therefore, according to the present embodiment, it is possible to cause image quality of an image obtained by performing image pickup of light from the object to be image quality suitable for diagnosis both in the distant view and in the near view.

Note that the image pickup system 1 of the present embodiment may not necessarily have a configuration for performing reading operations corresponding to the single pixel reading mode and the pixel addition reading mode in the light receiving portion 101. For example, the image pickup system 1 may have a configuration for performing signal processing corresponding to the single pixel reading mode and the pixel addition reading mode in the circuit substrate 94 or may have a configuration for performing image processing corresponding to the single pixel reading mode and the pixel addition reading mode in the image processing portion 42.

Further, according to the present embodiment, for example, the reading operation by the light receiving portion 101 and the signal processing by the circuit substrate 94 may be linked together in the pixel addition reading mode. More specifically, for example, it is conceivable that a reading operation for sequentially reading electric signals generated by a pixel group constituted by two pixels adjoining in a vertical direction (as indicated by the pixels P11 and P21, and the like in FIG. 5) as an electric signal corresponding to one pixel is performed by the light receiving portion 101, and such signal processing that electric signals corresponding two pixels adjoining in a horizontal direction among electric signals sequentially read by the light receiving portion 101 are added to make an electric signal corresponding to one pixel is performed by the circuit substrate 94, in the pixel addition reading mode.

Further, according to the present embodiment, the image pickup system 1 may not necessarily perform reading of electric signals in the state that a part of pixels of mutually adjoining pixel groups are overlapped, in the pixel addition reading mode. For example, the image pickup system 1 may perform reading of electric signals in a state that mutually adjoining pixel groups are not overlapped.

Second Embodiment

Figure 6:
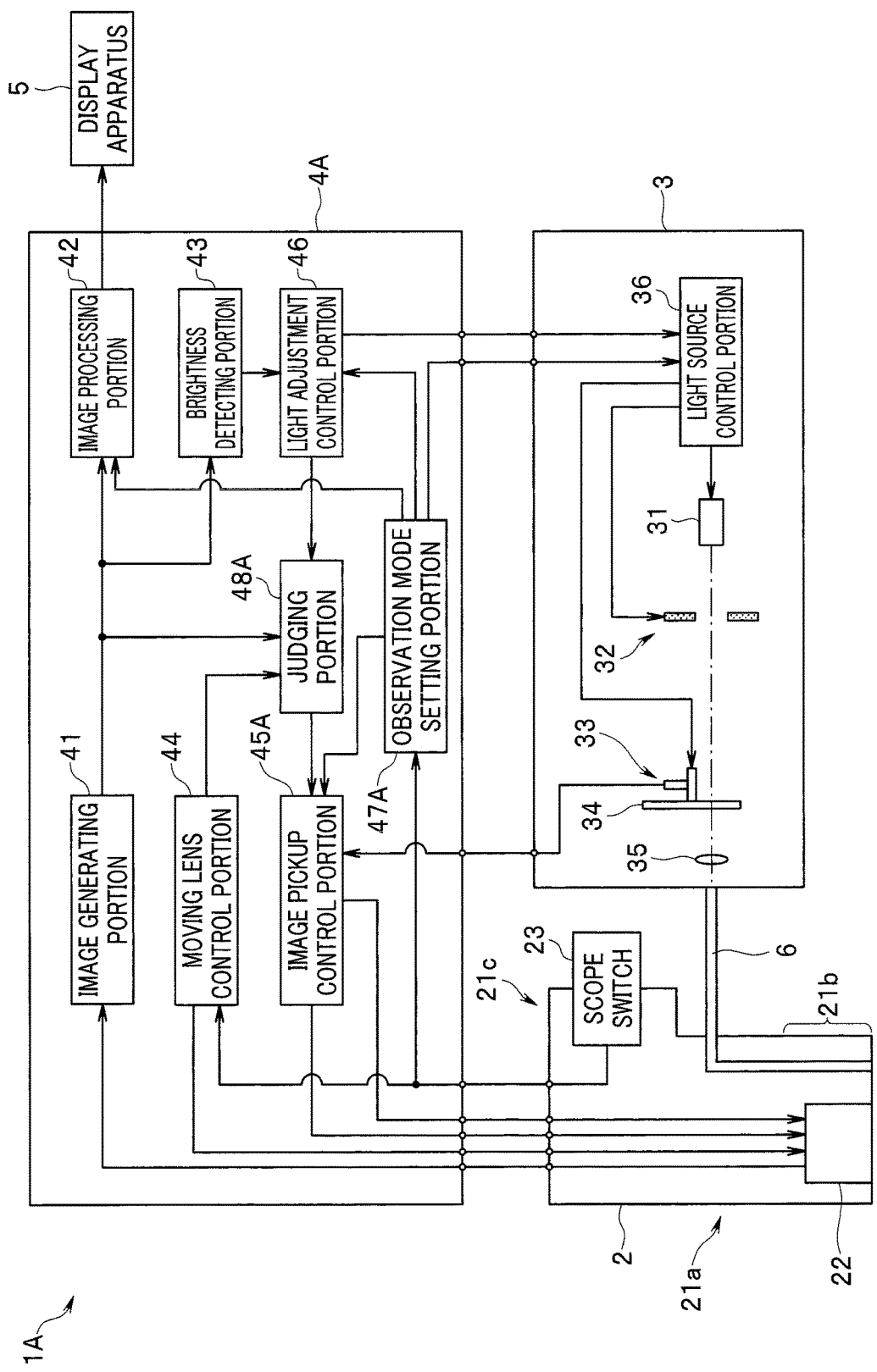
FIG. 6 is a diagram showing a configuration of a main part of an image pickup system according to a second embodiment.
Figure 7:
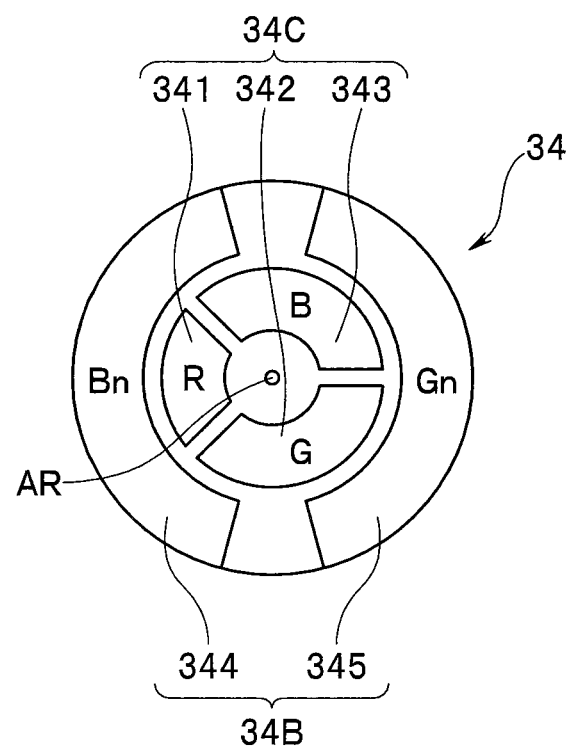
FIG. 7 is a diagram showing an example of the configuration of the rotating filter different from the example of FIG. 4.

FIGS. 6 and 7 relate to a second embodiment of the present invention.

Note that, in the present embodiment, detailed description of portions having configurations similar to those of the first embodiment will be omitted, and components having configurations and the like different from those of the first embodiment will be mainly described.

As shown in FIG. 6, an image pickup system 1A is configured having the endoscope 2, the light source apparatus 3, a processor 4A and the display apparatus 5. FIG. 6 is a diagram showing a configuration of a main part of the image pickup system according to the second embodiment.

As shown in FIG. 6, the processor 4A is configured having the image generating portion 41, the image processing portion 42, the brightness detecting portion 43, the moving lens control portion 44, an image pickup control portion 45A, the light adjustment control portion 46, an observation mode setting portion 47A and a judging portion 48A.

The image pickup control portion 45A is configured to detect which of the white light observation mode and the special light observation mode a current observation mode is, based on observation mode information outputted from the observation mode setting portion 47A.

The image pickup control portion 45A is configured to, when detecting that the current observation mode is the special light observation mode, perform an operation similar to the operation of the image pickup control portion 45 of the first embodiment, according to a judgment result obtained by the judgment process of the judging portion 48. Further, the image pickup control portion 45A is configured to, when the judgment result that the object is observed in the near view is obtained by the judging portion 48, perform an operation similar to that of the image pickup control portion 45 of the first embodiment.

On the other hand, the image pickup control portion 45A is configured to, when the image pickup control portion 45A detects that the current observation mode is the white light observation mode, and the judgment result that the object is observed in the distant view is obtained by the judging portion 48, detect a rotation state of the rotating filter 34, for example, based on a motor rotation amount, a motor rotation angle or the like of the filter driving mechanism 33, and furthermore detect which of R light, G light and B light the light emitted via a first filter group 34A is, based on the detected rotation state of the rotating filter 34. That is, the image pickup control portion 45A is configured to detect which of R light, G light and B light the light emitted from the light source apparatus 3 as illumination light for illuminating the object is.

The image pickup control portion 45A is configured to, when detecting that the light emitted via the first filter group 34A is G light or B light, perform control for setting the reading mode of the light receiving portion 101 to a single pixel reading mode for performing a reading operation similar to that of the first embodiment. Further, the image pickup control portion 45A is configured to, when detecting that the light emitted via the first filter group 34A is R light, perform control for setting the reading mode of the light receiving portion 101 to a pixel addition reading mode for performing a reading operation described later.

Note that the image pickup control portion 45A of the present embodiment may not necessarily be configured as described above. For example, the image pickup control portion 45A may be configured to perform the control for setting the reading mode of the light receiving portion 101 to the single pixel reading mode in synchronization with emission of G light or B light from the light source apparatus 3, and perform the control for setting the reading mode of the light receiving portion 101 to the pixel addition reading mode in synchronization with emission of R light from the light source apparatus 3.

The observation mode setting portion 47A is configured to detect a current observation mode set by the lens observation mode setting switch of the scope switch 23 and perform the control for causing the light source control portion 36, the image processing portion 42 and the light adjustment control portion 46 to perform operations corresponding to the detected current observation mode. Further, the observation mode setting portion 47A is configured to detect the current observation mode set by the lens observation mode setting switch of the scope switch 23 and output observation mode information showing the detected current observation mode to the image pickup control portion 45A.

The judging portion 48A is configured to perform a process similar to the process described in the first embodiment as the judgment process for judging: the object is observed in which of the distant view and the near view, based on any of the following: the images outputted from the image generating portion 41, the lens position information outputted from the moving lens control portion 44, the aperture amount information outputted from the light adjustment control portion 46 and the rotation speed information outputted from the light adjustment control portion 46. Further, the judging portion 48A is configured to output a judgment result obtained by the judgment process described above to the image pickup control portion 45A.

Next, operation of the image pickup system 1A provided with the configuration as described above will be described.

After powering on each portion of the image pickup system 1A, the user such as a surgeon arranges the distal end portion 21b at a position where it is possible to pick up images of a desired object in a body cavity of a subject and performs observation of the desired object in a state that the white light observation mode is set, by inserting the insertion portion 21a into the body cavity of the subject while confirming an image displayed on the display apparatus 5. Then, in response to such a user operation, R light, G light and B light are sequentially radiated to the desired object from the distal end portion 21b as illumination light; image pickup signals are generated by picking up images of return light from the desired object illuminated by the illumination light; the generated image pickup signals are outputted to the image generating portion 41 from the image pickup unit 22; and images generated by performing predetermined signal processing for the image pickup signals are outputted from the image generating portion 41 to the image processing portion 42, the brightness detecting portion 43 and the judging portion 48A.

The judging portion 48A performs the judgment process for judging: the object is observed in which of the distant view and the near view, based on any of the following: the images outputted from the image generating portion 41, the lens position information outputted from the moving lens control portion 44, the aperture amount information outputted from the light adjustment control portion 46 and the rotation speed information outputted from the light adjustment control portion 46.

When the object is observed in the near view according to a judgment result obtained by the judgment process of the judging portion 48A, the image pickup control portion 45A performs the control for setting the reading mode of the light receiving portion 101 of the image pickup device 92 to the single pixel reading mode.

Further, when the judgment result that the object is observed in the distant view is obtained by the judging portion 48A, the image pickup control portion 45A detects the rotation state of the rotating filter 34 based on a motor rotation amount, a motor rotation angle or the like of the filter driving mechanism 33, and further detects which of R light, G light and B light the light emitted via the first filter group 34A is, based on the detected rotation state of the rotating filter 34.

When detecting that the light emitted via the first filter group 34A is G light or B light, the image pickup control portion 45A performs the control for setting the reading mode of the light receiving portion 101 to a single pixel reading mode for performing a reading operation similar to that of the first embodiment. Further, the image pickup control portion 45A is configured to, when detecting that the light emitted via the first filter group 34A is R light, perform control for setting the reading mode of the light receiving portion 101 to the pixel addition reading mode for performing a reading operation as described below.

Here, a specific example of the reading operation of the pixel addition reading mode set according to control of the image pickup control portion 45A will be described below. Note that, in the description below, the case where the light receiving portion 101 is provided with the sixteen pixels P11 to P44 arranged as shown in FIG. 5, that is, the case where the light receiving portion 101 is constituted by 4×4 pixels will be described as an example for simplification. Further, in the present embodiment, reading operations suitable for the number of pixels of the light receiving portion 101 may be caused to be performed by appropriately modifying the reading operations described below.

The light receiving portion 101 performs, for example, an operation for sequentially reading electric signals generated by one pixel group constituted by a plurality of pixels arranged being mutually adjoining one another, as an electric signal corresponding to one pixel, as the reading operation of the pixel addition reading mode, according to control of the image pickup control portion 45A. It is assumed that, in the pixel addition reading mode set according to the control of the image pickup control portion 45A, reading of the electric signals is performed in the state that mutually adjoining pixel groups are not overlapped.

More specifically, as the reading operation of the pixel addition reading mode, the light receiving portion 101 performs, for example, the operation of adding electric signals generated by the pixel group constituted by the four pixels P11, P12, P21 and P22 and reading a result as an electric signal corresponding to one pixel, adding electric signals generated by the pixel group constituted by the four pixels P13, P14, P23 and P24 and reading a result as an electric signal corresponding to one pixel, adding electric signals generated by the pixel group constituted by the four pixels P31, P32, P41 and P42 and reading a result as an electric signal corresponding to one pixel and adding electric signals generated by the pixel group constituted by the four pixels P33, P34, P43 and P44 and reading a result as an electric signal corresponding to one pixel. That is, according to such a reading operation of the pixel addition reading mode, reading of electric signals corresponding to one frame is completed at a timing of having added the electric signals generated by a pixel group constituted by the four pixels P33, P34, P43 and P44 and read a result as an electric signal corresponding to one pixel.

Here, according to the controls as described above, for example, when image pickup is performed for a biological mucosal surface layer as the object, an image GI and an image BI with a resolving power making it possible to identify a structure of microvessels existing on the biological mucosal surface layer are generated, and an image RI with brightness making it possible to visually confirm the structure of the microvessels is generated. Therefore, according to the controls as described above, for example, it is possible to, while suppressing deterioration of information about the microvessels existing on a biological mucosal surface layer, cause an image with brightness suitable for observation of the microvessels to be displayed on the display apparatus 5.

Note that, according to the present embodiment, for example, it is also conceivable to, when detecting that light emitted via the first filter group 34A is B light, perform the control for setting the reading mode of the light receiving portion 101 to the single pixel reading mode for performing a reading operation similar to the first embodiment and, when detecting that the light emitted via the first filter group 34A is R light or G light, perform the control for setting the reading mode of the light receiving portion 101 to the pixel addition reading mode for performing the reading operation as described above. According to such control, for example, it is possible to, while suppressing deterioration information about microvessels existing on a biological mucosal surface layer, cause an image with brightness suitable for observation of the microvessels to be displayed on the display apparatus 5.

Further, according to the present embodiment, for example, it is also conceivable to, when detecting that light emitted via the first filter group 34A is G light, perform the control for setting the reading mode of the light receiving portion 101 to the single pixel reading mode for performing a reading operation similar to the first embodiment and, when detecting that the light emitted via the first filter group 34A is B light or R light, perform the control for setting the reading mode of the light receiving portion 101 to the pixel addition reading mode for performing the reading operation as described above. According to such control, for example, it is possible to, while suppressing deterioration information about microvessels with a characteristic structure existing on a biological mucosal surface layer, cause an image with brightness suitable for observation of the microvessels to be displayed on the display apparatus 5.

As described above, according to the present embodiment, when a current observation mode is the white light observation mode, and the object is observed in the distant view, an operation for switching the reading mode of the light receiving portion 101 is performed according to light emitted via the first filter group 34A. Therefore, according to the present embodiment, when the current observation mode is the white light observation mode, and the object is observed in the distance view, it is possible to cause such an observation image with a high S/N and a high resolution that is provided with brightness and a resolving power suitable, for example, for identifying the object such as a lesion existing in the body cavity of the subject to be displayed on the display apparatus 5.

Note that, according to the present embodiment, the image pickup system 1 may not perform reading of electric signals in the state that mutually adjoining pixel groups are not overlapped in the pixel addition reading mode. For example, the image pickup system 1 may perform reading of electric signals in the state that a part of pixels of mutually adjoining pixel groups are overlapped.

Further, in the present embodiment, for example, a first filter group 34C as shown in FIG. 7 may be provided instead of the first filter group 34A to configure the rotating filter 34. FIG. 7 is a diagram showing an example of the configuration of the rotating filter different from the example of FIG. 4.

The first filter group 34C is formed so that an area ratio of the R filter 341 configured to cause R light to be transmitted, the G filter 342 configured to cause G light to be transmitted and the B filter 343 configured to cause B light to be transmitted becomes 1:FG:FB. It is assumed that each of FG and FB described above is a predetermined value equal to or larger than two. That is, according to such a configuration of the first filter group 34C, each of G light and B light can be emitted in an emission time period equal to or more than twice an emission time period of R light.

On the other hand, when the rotating filter 34 is provided with the first filter group 34C, the current observation mode is the white light observation mode, and the object is observed in the distant view, the image processing portion 42 generates an RGB color image by combining the image RI, the image GI and the image BI.

Figure 8:
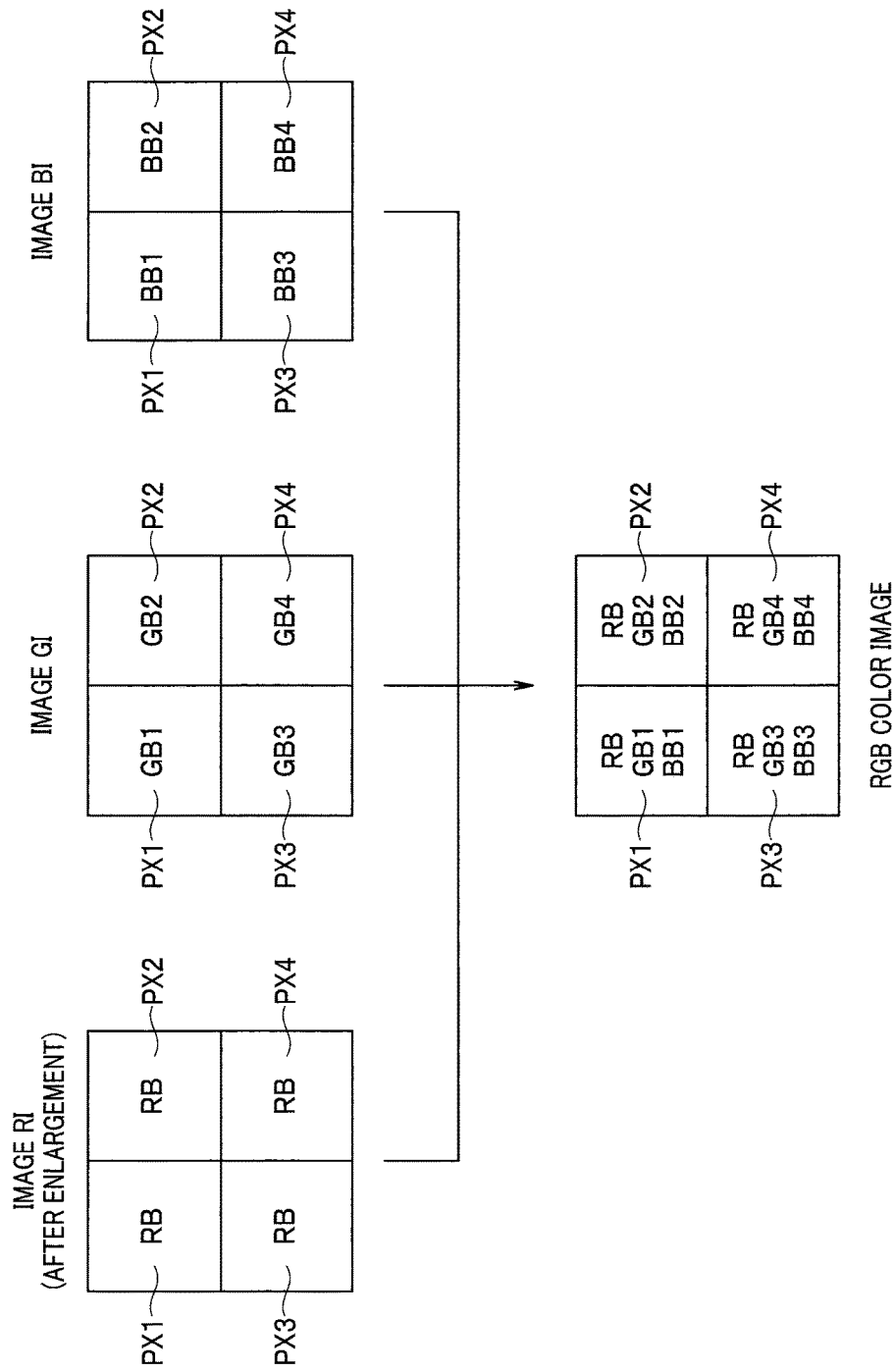
FIG. 8 is a diagram for illustrating an example of a process performed in an image processing portion.

Here, for example, when a reading operation of adding electric signal generated by groups of pixels each of which is constituted by mutually adjoining four pixels and reading a result as an electric signal corresponding to one pixel is performed in the pixel addition reading mode, the image processing portion 42 generates the RGB color image by performing a process for increasing a size of the image RI by a factor of four and further combining the enlarged image RI, the image GI and the image BI. FIG. 8 is a diagram for illustrating an example of the process performed in the image processing portion.

According to the process of the image processing portion 42 as described above, luminance values of four mutually adjoining pixels PX1 to PX4 become a same luminance value RB in the image RI after enlargement, for example, as shown in FIG. 8. Further, according to the process of the image processing portion 42 as described above, pixel values of the pixel PX1 are RB, GB1 and BB1, pixel values of the pixel PX2 are RB, GB2 and BB2, pixel values of the pixel PX3 are RB, GB3 and BB3, and pixel values of the pixel PX4 are RB, GB4 and BB4 in the RGB color image, for example, as shown in FIG. 8.

Therefore, by configuring the rotating filter 34 by providing the first filter group 34C instead of the first filter group 34A, it is possible to, when the current observation mode is the white light observation mode, and the object is observed in the distant view, further improve the S/N of an observation image displayed on the display apparatus 5.

Further, according to the present embodiment, for example, by adding an IR filter provided with such an optical characteristic that causes IR light, which is near-infrared light, to be transmitted to configure the first filter group 34A, R light, G light, B light and IR light are sequentially emitted from the light source apparatus 3. Further, according to the present embodiment, for example, it is also conceivable to, when the object is observed in the distant view, and it is detected that light emitted via the first filter group 34A is B light or G light, perform the control for setting the observation mode of the light receiving portion 101 to the single pixel reading mode and, when the object is observed in the distant view, and it is detected that the light emitted via the first filter group 34A is R light or IR light, perform the control for the reading mode of the light receiving portion 101 to the pixel addition reading mode, according to the configuration of the first filter group 34A as described above. According to such control, for example, it is possible to cause an image including a large-diameter blood vessel existing in a biological mucosal depth to be displayed on the display apparatus 5, and, as a result, it is possible to prevent damage of the blood vessel in treatment using an electrosurgical knife and the like.

Note that the present invention is not limited to each of the embodiments described above, and it is possible to make various changes and applications within a range not departing from the spirit of the invention as a matter of course.

What is claimed is:

1. An image pickup system comprising:
   a light source apparatus configured to sequentially emit lights with a plurality of mutually different wavelength bands as illumination light for illuminating an object;
   an objective optical system configured to form an image of light from the object illuminated by the illumination light;
   an image pickup device provided with an image pickup surface formed by two-dimensionally arranging a plurality of pixels for receiving the light formed by the objective optical system and photoelectrically converting the received light to generate electric signals;
   a judging portion configured to perform a judgment process for judging: the object is observed in which of a distant view and a near view; and
   an image pickup control portion configured to perform control for setting a reading mode of the image pickup device to either a single pixel reading mode which is a mode for sequentially reading the electric signals generated by the respective pixels arranged on the image pickup surface one by one, or a pixel addition reading mode which is a mode for, with electric signals generated by one pixel group constituted by a plurality of pixels arranged mutually adjoining one another on the image pickup surface as electric signals corresponding to one pixel, sequentially reading the electric signals corresponding to one pixel, according to a judgment result obtained by the judgment process of the judging portion; wherein
   the light source apparatus is configured to be able to sequentially emit light of a red wavelength band, light of a green wavelength band and light of a blue wavelength band as the illumination light; and
   the image pickup control portion performs control for setting the reading mode of the image pickup device to the single pixel reading mode when a judgment result that the object is observed in the distant view is obtained, and it is detected that the light of the blue wavelength band is emitted from the light source apparatus as the illumination light; and performs control for setting the reading mode of the image pickup device to the pixel addition reading mode when the judgment result that the object is observed in the distant view is obtained, and it is detected that the light of the red wavelength band is emitted from the light source apparatus as the illumination light.

2. The image pickup system according to claim 1, wherein, when the reading mode of the image pickup device is set to the pixel addition reading mode, the image pickup control portion performs control for causing reading of the electric signals to be performed in a state that a part of pixels of mutually adjoining pixel groups are overlapped on the image pickup surface.

3. The image pickup system according to claim 1, wherein, when the reading mode of the image pickup device is set to the pixel addition reading mode, the image pickup control portion performs control for causing reading of the electric signals to be performed in a state that mutually adjoining pixel groups are not overlapped on the image pickup surface.

4. The image pickup system according to claim 1, wherein the judging portion judges: the object is observed in which of the distant view and the near view, by detecting output values of the electric signals read from the image pickup device.

5. The image pickup system according to claim 4, wherein
   an outer edge portion of the image pickup surface is provided with a light blocking portion configured including an opening formed to cause the light formed by the objective optical system to pass through and a light blocking member formed to block the light formed by the objective optical system; and
   the judging portion judges: the object is observed in which of the distant view and the near view, by detecting output values of electric signals read from pixels or pixel groups positioned at the opening.

6. The image pickup system according to claim 1, further comprising a moving lens provided in the objective optical system and configured to be able to move along a direction of an optical axis of the objective optical system; wherein
   the judging portion judges: the object is observed in which of the distant view and the near view, by detecting a current arrangement position of the moving lens.

7. The image pickup system according to claim 6, further comprising:
   an optical indicator provided on an outer edge portion of a light incident surface of the moving lens; and
   an image generating portion configured to generate images corresponding to the electric signals outputted from the image pickup device; wherein
   the judging portion judges: the object is observed in which of the distant view and the near view, by detecting whether or not the optical indicator is included in the images generated by the image generating portion.

8. The image pickup system according to claim 1, further comprising a light adjustment control portion configured to perform control for adjusting a light amount of the illumination light emitted from the light source apparatus and output control information showing a current control state in adjustment of the light amount of the illumination light; wherein
   the judging portion judges: the object is observed in which of the distant view and the near view, based on the control information outputted from the light adjustment control portion.

9. The image pickup system according to claim 8, wherein
   the light source apparatus comprises an aperture device configured to be able to adjust the light amount of the illumination light to a light amount corresponding to an aperture amount; and
   the light adjustment control portion controls the aperture device to adjust the light amount of the illumination light and outputs information showing a current aperture amount of the aperture device as the control information.

10. The image pickup system according to claim 8, wherein
    the light source apparatus comprises a light source configured to be able to adjust the light amount of the illumination light to a light amount corresponding to a magnitude of a driving current; and
    the light adjustment control portion controls the light source to adjust the light amount of the illumination light and outputs information showing a magnitude of a driving current currently supplied to the light source as the control information.

11. The image pickup system according to claim 1, further comprising an aperture device configured to be able to adjust a light amount of the light formed on the image pickup device via the objective optical system to a light amount corresponding to an aperture amount; wherein
    the image pickup control portion performs control for causing the aperture amount of the aperture device to change according to the judgment result obtained by the judgment process of the judging portion.

12. The image pickup system according to claim 1, wherein
    the light source apparatus is further configured to be able to switch the lights sequentially emitted as the illumination light to either broadband lights of a plurality of colors or narrowband lights of a plurality of colors; and
    when detecting that light emitted from the light source apparatus is the narrowband lights, the judging portion obtains a judgment result that the object is observed in the near view.

13. The image pickup system according to claim 1, wherein the light source apparatus is configured to emit the light of the blue wavelength band in an emission time period equal to or more than twice an emission time period of the light of the red wavelength band.

14. The image pickup system according to claim 1, wherein, when the judgment result that the object is observed in the distant view is obtained, and it is detected that the light of the red wavelength band or the light of the green wavelength band is emitted from the light source apparatus as the illumination light, the image pickup control portion performs the control for setting the reading mode of the image pickup device to the pixel addition reading mode.

15. The image pickup system according to claim 1, wherein
    the light source apparatus is configured to sequentially emit the light of the red wavelength band, the light of the green wavelength band, the light of the blue wavelength band and near-infrared light as the illumination light; and
    the image pickup control portion performs the control for setting the reading mode of the image pickup device to the single pixel reading mode when the judgment result that the object is observed in the distant view is obtained, and it is detected that the light of the green wavelength band or the light of the blue wavelength band is emitted from the light source apparatus as the illumination light; and performs the control for setting the reading mode of the image pickup device to the pixel addition reading mode when the judgment result that the object is observed in the distant view is obtained, and it is detected that the light of the red wavelength band or the near-infrared light is emitted from the light source apparatus as the illumination light.

16. The image pickup system according to claim 1, wherein the objective optical system and the image pickup device are provided on a distal end portion of an endoscope insertion portion configured to be inserted into a body cavity of a subject.

17. An image pickup system comprising:
a light source apparatus configured to sequentially emit lights with a plurality of mutually different wavelength bands as illumination light for illuminating an object;
an objective optical system configured to form an image of light from the object illuminated by the illumination light;
an image pickup device provided with an image pickup surface formed by two-dimensionally arranging a plurality of pixels for receiving the light formed by the objective optical system and photoelectrically converting the received light to generate electric signals;
a judging portion configured to perform a judgment process for judging: the object is observed in which of a distant view and a near view; and
an image pickup control portion configured to perform control for setting a reading mode of the image pickup device to either a single pixel reading mode which is a mode for sequentially reading the electric signals generated by the respective pixels arranged on the image pickup surface one by one, or a pixel addition reading mode which is a mode for, with electric signals generated by one pixel group constituted by a plurality of pixels arranged mutually adjoining one another on the image pickup surface as electric signals corresponding to one pixel, sequentially reading the electric signals corresponding to one pixel, according to a judgment result obtained by the judgment process of the judging portion; wherein
the light source apparatus is configured to be able to sequentially emit light of a red wavelength band, light of a green wavelength band and light of a blue wavelength band as the illumination light; and
the image pickup control portion performs control for setting the reading mode of the image pickup device to the single pixel reading mode when a judgment result that the object is observed in the distant view is obtained, and it is detected that the light of the green wavelength band or the light of the blue wavelength band is emitted from the light source apparatus as the illumination light; and performs control for setting the reading mode of the image pickup device to the pixel addition reading mode when the judgment result that the object is observed in the distant view is obtained, and it is detected that the light of the red wavelength band is emitted from the light source apparatus as the illumination light.

18. The image pickup system according to claim 17, wherein the light source apparatus is configured to emit each of the light of the green wavelength band and the light of the blue wavelength band in an emission time period equal to or more than twice an emission time period of the light of the red wavelength band.

* * * * *